(12) United States Patent
Deutinger

(10) Patent No.: US 11,039,802 B2
(45) Date of Patent: Jun. 22, 2021

(54) METHOD FOR PRODUCING A MICROSTRUCTURE COMPONENT, MICROSTRUCTURE COMPONENT AND X-RAY DEVICE

(71) Applicant: Siemens Healthcare GmbH, Erlangen (DE)

(72) Inventor: Andrea Deutinger, Forstern (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 91 days.

(21) Appl. No.: 16/281,189

(22) Filed: Feb. 21, 2019

(65) Prior Publication Data

US 2019/0261936 A1   Aug. 29, 2019

(30) Foreign Application Priority Data

Feb. 28, 2018 (EP) .................... 18159242

(51) Int. Cl.
*A61B 6/00* (2006.01)
*G21K 1/02* (2006.01)
(Continued)

(52) U.S. Cl.
CPC ............ *A61B 6/484* (2013.01); *A61B 6/4035* (2013.01); *G01N 23/083* (2013.01);
(Continued)

(58) Field of Classification Search
CPC ..... A61B 6/4035; A61B 6/4291; A61B 6/484; G02B 2005/1804; G02B 5/1838;
(Continued)

(56) References Cited

U.S. PATENT DOCUMENTS 8,223,924 B2   7/2012  Borner et al.
2011/0052800 A1*  3/2011  Setomoto ......... B29D 11/00769
                                                                       427/162
(Continued)

FOREIGN PATENT DOCUMENTS

CN   101813796 B   7/2012
DE   102010017425 A1   12/2011
(Continued)

OTHER PUBLICATIONS

Translation of JP2015121639 (Year: 2015).*
(Continued)

*Primary Examiner* — Matthew P Travers
(74) *Attorney, Agent, or Firm* — Harness, Dickey & Pierce, P.L.C.

(57) ABSTRACT

In a method for producing a microstructure component, which is used in particular as an x-ray phase contrast grating in an x-ray device, a material absorbing x-rays is poured into a mold able at least to be deformed about one bending axis, which is formed by a silicon substrate and which has a plurality of cutouts running in a direction of the thickness of the silicon substrate with dimensions in the micrometer range. The mold into which the material is poured is heated up to a working temperature value lying above the room temperature and below a melting temperature value of the material which is poured into it and is formed into a final contour as per specifications.

20 Claims, 4 Drawing Sheets

(51) Int. Cl.
  *G21K 1/06* (2006.01)
  *G02B 5/18* (2006.01)
  *G01N 23/083* (2018.01)

(52) U.S. Cl.
  CPC ......... *G02B 5/1838* (2013.01); *G02B 5/1847* (2013.01); *G02B 5/1852* (2013.01); *G02B 5/1857* (2013.01); *G21K 1/025* (2013.01); *G21K 1/06* (2013.01); *G21K 2207/005* (2013.01)

(58) Field of Classification Search
  CPC ....... G02B 5/1847–1857; G02B 5/1866–1871; G21K 1/06; G21K 2207/005
  See application file for complete search history.

(56) References Cited

U.S. PATENT DOCUMENTS

| | | |
|---|---|---|
| 2012/0219916 A1 | 8/2012 | Teshima et al. |
| 2012/0263274 A1 | 10/2012 | Ouchi |
| 2013/0148780 A1 | 6/2013 | Mohr et al. |
| 2013/0164457 A1* | 6/2013 | Ehlers ............ G21K 1/06 427/555 |
| 2013/0181130 A1 | 7/2013 | Itoh et al. |
| 2016/0265125 A1 | 9/2016 | Yokoyama |

FOREIGN PATENT DOCUMENTS

| | | |
|---|---|---|
| DE | 102010061481 A1 | 6/2012 |
| DE | 102015201741 A1 | 8/2016 |
| EP | 3054455 A1 | 8/2016 |
| JP | 3599325 B2 | 12/2004 |
| JP | 3627856 B2 | 3/2005 |
| JP | 2012132793 A | 7/2012 |
| JP | 2015121639 A | 7/2015 |
| WO | WO 2017036729 A1 | 3/2017 |

OTHER PUBLICATIONS

Translation of DE102015201741 (Year: 2016).*
Nitto "Thermal Release Sheet for Electronic Component Processing REVALPHA"; URL: https://www.nitto.com/us/en/products/group/e_parts/electronic/001/ (both in English and German), Nov. 16, 2018.

* cited by examiner

METHOD FOR PRODUCING A MICROSTRUCTURE COMPONENT, MICROSTRUCTURE COMPONENT AND X-RAY DEVICE

PRIORITY STATEMENT

The present application hereby claims priority under 35 U.S.C. § 119 to European patent application number EP 18159242.9 filed Feb. 28, 2018, the entire contents of which are hereby incorporated herein by reference.

FIELD

Embodiments of the invention generally relate to a method for producing a microstructure component, in particular an x-ray phase contrast grating; to a microstructure component, in particular to an x-ray phase contrast grating; and also to an x-ray device with such a grating.

BACKGROUND

In the area of x-ray imaging, in particular in the medical area, what is referred to as the Talbot effect is used in some cases. This enables more precise image information to be generated, in that the contrast of the images created is improved by incorporating a phase shift of the x-rays caused by an examination object. In such cases a so-called (x-ray) phase contrast grating is regularly used, with is introduced into the beam path. Such a grating is usually formed in this case by lamellae aligned in the direction of the x-ray radiation and made from an x-ray absorbing material. Usually the wall thickness and the distances of these lamellae from one another lie in the one- to low two-digit millimeter range. Also the thickness (or: height) of the grating as a whole in the irradiated area usually lies at a maximum of one millimeter. Thus such a contrast phase grating involves a microstructure component.

Because of the small dimensions, these phase contrast gratings are mostly produced by etching methods in silicon wafers and subsequent filling of the etched recesses with x-ray absorbing material, in particular a metal or a metal alloy, for embodying the lamellae. This is known for example from DE 10 2015 201 741 A1.

SUMMARY

The inventors have discovered that frequently, the problem is that the phase contrast grating should ideally be tailored to the local radiation direction of the radial rays emanating from a mostly punctiform radiation source. I.e. the lamellae should ideally be placed at an angle to one another.

At least one embodiment of the invention makes an improved microstructure component possible.

At least one embodiment of the invention is directed to a method for producing a microstructure component. Furthermore at least one embodiment of the invention is directed to a microstructure component. Moreover at least one embodiment of the invention is directed to an x-ray device. Forms of embodiment and developments of the invention that are advantageous and in some cases inventive per se are set out in the claims and in the description given below.

At least one embodiment of the inventive method serves to produce a microstructure component, in particular an (x-ray) phase contrast grating. In accordance with at least one embodiment of the method, an (in particular elastic) mold at least able to be deformed about a bending axis, which is formed by a silicon substrate and which has a plurality of cutouts running in a direction of the thickness of the silicon substrate, has a material that absorbs x-rays poured into it. The cutouts in this case have dimensions in the micrometer range (i.e. in particular seen in the surface direction the smallest dimensions amount to around up to 10 micrometers, in particular around 0.5, 1 or up to 4 micrometers). The mold into which the material is poured is heated up to a working temperature value lying above room temperature and below a melting temperature value of the filler material and subsequently formed into a final contour as per specifications.

At least one embodiment of the invention is directed to a method for producing a microstructure component, the method comprising:

pouring a material for absorbing x-rays into a mold, the mold being at least deformable about a bending axis, formed by a silicon substrate, and including a plurality of cutouts running in a thickness direction of the silicon substrate with dimensions in the micrometer range;

heating up the mold, including the material poured into the mold, to a working temperature value above a room temperature and below a melting temperature value of the material poured into the mold; and deforming the mold, with the material poured into the mold, into a final contour according to specifications.

At least one embodiment of the inventive microstructure component in particular represents the aforesaid phase contrast grating and is produced in accordance with the method described above. I.e. the microstructure component likewise has the physical features and advantages described above, in particular those produced by the method of production.

At least one embodiment of the inventive x-ray device has the phase contrast grating formed by the microstructure component described above, and thus likewise shares the features and advantages described above.

BRIEF DESCRIPTION OF THE DRAWINGS

Example embodiments of the invention will be described below, in greater detail with reference to a drawing. In the figures.

Parts corresponding to one another are always labeled with the same reference characters in all figures

DETAILED DESCRIPTION OF THE EXAMPLE EMBODIMENTS

Figure 1:
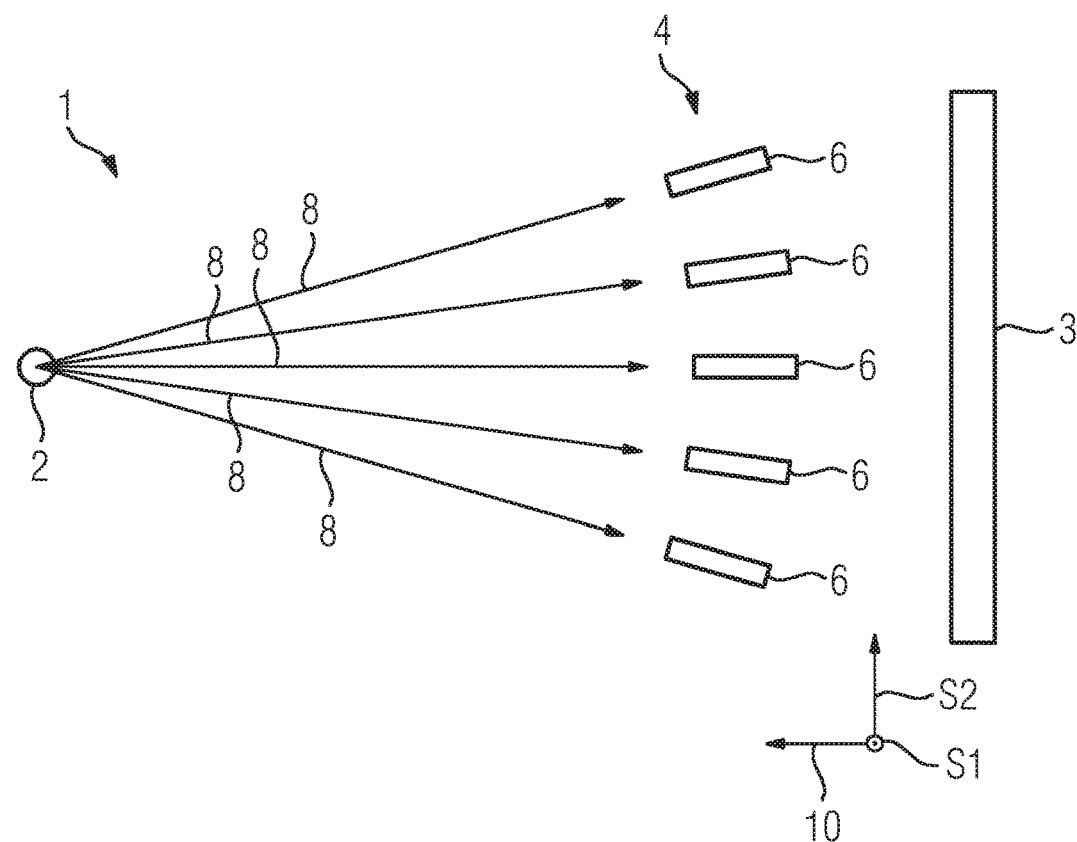
FIG. 1 shows an x-ray device with a phase contrast grating, in a schematic side view.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules.

Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the inventive method serves to produce a microstructure component, in particular an (x-ray) phase contrast grating. In accordance with at least one embodiment of the method, an (in particular elastic) mold at least able to be deformed about a bending axis, which is formed by a silicon substrate and which has a plurality of cutouts running in a direction of the thickness of the silicon substrate, has a material that absorbs x-rays poured into it. The cutouts in this case have dimensions in the micrometer range (i.e. in particular seen in the surface direction the smallest dimensions amount to around up to 10 micrometers, in particular around 0.5, 1 or up to 4 micrometers). The mold into which the material is poured is heated up to a working temperature value lying above room temperature and below a melting temperature value of the filler material and subsequently formed into a final contour as per specifications.

The fact that the deformation of the mold filled with the material is undertaken below the melting temperature of the material advantageously prevents the material melting and, in its melted state, being able to escape from the cutouts. Furthermore a filling of the mold, in concrete terms of the cutouts, before the deformation into the final contour is regularly simpler than filling an already pre-formed mold.

Especially preferably the "filled" mold, i.e. the mold filled with the material, will be deformed to the final contour as per specifications at a working temperature value under (in particular temperature-supported) creep of the filler material. Creep (or also: "retardation") is understood in particular in this case as at least a change in structure, which proceeds comparatively slowly and mostly under a comparatively small load and leads to a plastic deformation. Mostly the processes that lead to such a change in structure are thermally activated (in particular in metals) i.e. only as from a temperature mostly increased compared to room temperature. The exploitation of the creep of the filler material described here advantageously makes it possible to deform the filled mold into the final contour with comparatively low reformation forces. This advantageously enables a risk of damaging the microstructures of the microstructure component and/or the mold, and thus that the precision of the microstructure component will be reduced, to be lowered.

Preferably a metal (preferably with a comparatively high tendency to creep), for example tin or a tin alloy, is in particular employed as the x-ray-absorbing material.

In a preferred embodiment of the method, a value of around 20-50 percent, in particular of around 30-40 percent of the melting temperature value of the x ray absorbing material is employed as the working temperature value. In particular the working temperature value at least involves the value of a so called transition temperature, as from which structural mechanisms of the material (in particular of the metal) take place with thermal activation. As from this temperature value the tendency to creep, in particular of metallic materials, increases. Regularly in such cases there is already a plastic deformation at stresses (stress values) introduced into the material, which lie below an expansion limit of the material. Especially preferably the x ray absorbing material, in particular the metal or a metal alloy, is chosen in this case such that the deformation occurs by creep at a working temperature value and stress values that advantageously do not lead to damage to the structure of the mold. Thus the mold with the x ray absorbing material poured into it is advantageously able to be deformed with loads that are low enough so that, at temperature values lying below the working temperature value, in particular at room temperature, they would merely lead to an elastic deformation.

In an expedient embodiment of the method, the x-ray-absorbing material will be introduced in a molten state into the mold, in particular into the cutouts. In particular a die casting method is used in this case. Through the pouring-in of the molten material a mechanical interaction between the mold and the filler material is reduced, so that in turn the risk of damaging the microstructures of the mold is reduced. In particular by the use of pressure, a filling of the mold that is as complete as possible and thus a precise remolding of the microstructures is made possible.

In an especially expedient embodiment of the method, the silicon substrate of the mold is pre-treated before the introduction of the x-ray-absorbing material to avoid a chemical bonding of the material with the silicon substrate. For example the silicon substrate—preferably all surfaces, which according to specifications come into contact with the material to be introduced—is conditioned (for example with a solution, plasma or the like) or coated (for example by way of sputtering, PVD, CVD or the like). This makes it possible for the mold, in an optional method step after (or alternatively also before) the deformation, to be able to be at least partly removed, so that the material with which the cutouts are filled remains as an individual column, lamella or the like at least for the most part.

In a further expedient embodiment of the method, the mold with the material poured into it is deformed via a tool, which has a lower shell and an upper shell with mirror-image mold surfaces curved in each case along a circular cylindrical surface (the mold surfaces are thus each curved in the same direction and, in the state in which the mold is used as per specification, are thus parallel to one another). In particular the filled mold will be inserted between the lower shell and the upper shell and the upper shell subsequently loaded with a force required for "creep remolding".

Preferably, for deformation in particular by way of the upper shell described above, a force (also referred to as the "closing force") is exerted on the mold, which in particular corresponds to a mass of 10-150 grams, preferably of 20-100 grams. Such a force is in particular sufficient for dimensions of the microstructure component in the thickness direction of less than a millimeter, in particular in the range of up to around 500 micrometers, for creep reformation while avoiding damaging the microstructures of the mold.

In a embodiment of the method, expedient for production technology the deformation of the filled mold is carried out in an oven, in particular a circulating air oven, in which the heating up to the working temperature value takes place. Preferably in this case the filled mold is inserted into the tool described above, loaded with the corresponding force and subsequently put into the oven. In the oven the tool and thus also the mold inserted therein heat up to the working temperature value, so that, as a result of the applied force, the x-ray-absorbing material is molded by creep in particular to the final contour predetermined by the tool. Preferably the mold is embodied elastically in this case such that it follows elastically the deformation of the material with which it is filled. Through the creep of the filler material however a plastic deformation of the material takes place, through which the mold itself retains the final contour achieved even after removal from the tool.

In a preferred embodiment of the method, the cutouts of the mold are formed by using etching to embody columns. These columns run in this case in a first substrate direction and are separated from one another by transverse webs, which run in a second substrate direction at right angles to the first substrate direction. Moreover the columns are also arranged next to one another in the form of rows in the second substrate direction, wherein the individual rows are separated from one another by longitudinal webs running in parallel to the columns. I.e. the columns are arranged in a grid, by the columns being arranged within the rows with their longitudinal direction in parallel to the first substrate direction and in the second substrate direction by a number of rows (in particular each with a number of columns) being arranged next to one another. Preferably in this case the entire silicon substrate is covered by the grid, at least in the first substrate direction. As a result of this alignment of the columns, a flexural strength of the silicon substrate (and thus of the mold) is advantageously reduced about a bending axis aligned in the first substrate direction. Preferably the (filled) mold is also deformed about this bending axis.

In an especially expedient development the columns described above, which follow one another in the second substrate direction, are arranged offset to one another in relation to their longitudinal extent along the first substrate direction. I.e. the columns are shifted from row to row in the first substrate direction. Preferably in this case the columns are shifted by half their longitudinal extent according to specification. The result of this is that the transverse webs described above, seen in the second substrate direction, are only flush with one another in every second row. Moreover the result of the shifting by half their longitudinal extent is an even and in particular symmetrical deformation during a bending about the bending axis described above.

In a further expedient embodiment of the method the cutouts, in particular the columns described above, are in particular molded out by an anisotropic etching method such that they penetrate the silicon substrate in the thickness direction. Thus the cutouts or columns are preferably opened to the silicon substrate on both sides.

Preferably, to embody the mold, in particular using etching technology, a plurality of point-type injection structures (preferably pyramid-shaped) and in particular separate from one another are inserted into the grid described above in a first surface of the in particular wafer-like silicon substrate (for example in a wafer or a part of a wafer). The injection structures are collected together in this case into groups in the first substrate direction, which are assigned to the respective cutout, preferably to each of the columns. The groups are spaced apart from one another in the first substrate direction for subsequent embodiment of the transverse webs. Following this the injection structures are lengthened into drilled holes in the depth direction (or also: thickness direction) of the silicon substrate in an etching step—i.e. deepened. Subsequently a second surface opposite to the first surface of the silicon substrate is at least partly removed in a further etching step for rear-side opening of the drilled holes. In a subsequent etching step an etching medium effective anisotropically—in particular an etching solution—is then poured alternately through the drilled holes from both surfaces of the silicon substrate, so that the (in particular initially round) drilled holes widen out (preferably to form a square cross-section) and connect themselves within the respective group to form the respective cutout, in particular to form the column running in the first substrate direction. Preferably the first surface of the silicon substrate is selected in this case such that it is aligned parallel to a "(100) crystal plane" of the silicon.

In a preferred embodiment of the method the cutouts, in particular the columns, are molded with an aspect ratio in the thickness direction of the silicon substrate of around 1:450. The cutouts or columns in this case have, in particular seen in the second substrate direction, dimensions (i.e. a width) of around one to four micrometers. These types of "fine" (i.e. small and filigree) structures are in particular advantageous for the use of the microstructure component as an (x-ray) phase contrast grating in an x-ray device. The lamellae of this phase contrast grating serving to absorb the x-rays will be formed in this case by the material absorbing the x-rays and inserted to fill the cutouts. Preferably the rows described above formed by the columns running in the first substrate direction lie at a distance of around 2-12 micrometers from one another. This corresponds in particular to a so-called grating constant of the phase contrast grating.

The columns described above are also preferably embodied with a longitudinal extent of between 20 and 1300, preferably between 50 and less than 1000 micrometers. In particular with values below 1000 (in particular up to 300) micrometers, on the one hand a flexural strength sufficiently low for deforming the filled mold but sufficiently high for handling (even the filled mold) is produced in particular about a bending axis lying in the first substrate direction.

In order to further lower the flexural strength of the filled mold for the deformation about this bending axis, in an optional method step before the deformation, in a (further) etching step a central area of the rear side (i.e. of the second surface) of the silicon substrate is removed except for a residual thickness and only terminating edge areas of the silicon substrate in the second substrate direction are left. In the central area in this case—as described above—the columns or lamellae formed by the filler material protrude from the silicon substrate. In particular for the use of the microstructure component as a phase contrast grating an absorption of the x-rays in the silicon is also reduced by this in the central area (which preferably corresponds to an irradiated area).

At least one embodiment of the inventive microstructure component in particular represents the aforesaid phase contrast grating and is produced in accordance with the method described above. I.e. the microstructure component likewise has the physical features and advantages described above, in particular those produced by the method of production.

At least one embodiment of the inventive x-ray device has the phase contrast grating formed by the microstructure component described above, and thus likewise shares the features and advantages described above.

Figure 2:
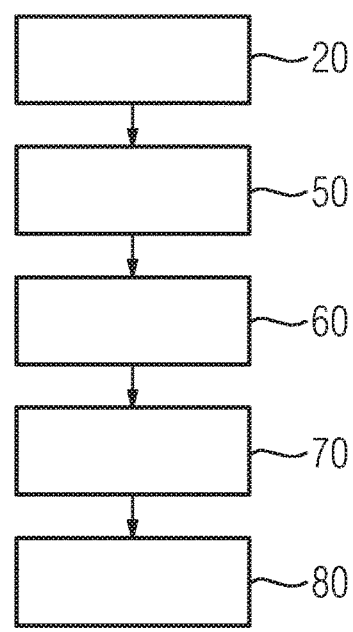
FIG. 2 shows a method for producing the phase contrast grating, in a schematic flow diagram.

Shown indicated schematically in FIG. 1 is an x-ray device 1. The x-ray device 1 has an x-ray source 2 and an x-ray detector 3. Arranged in the beam path between the x-ray source 2 and the x-ray detector 3 is an (x-ray) phase contrast grating 4. The phase contrast grating 4 in this figure has number of lamellae 6, which are aligned in parallel to the respective local x-ray part beam 8. The phase contrast grating 4 in this case, seen in the thickness direction 10 (or also: along the radiation direction) has dimensions of a maximum of one millimeter. Thus the phase contrast grating 4 involves a component with structures in the micrometer range ("microstructure component"). In order to still be able to mold the lamellae 6 of the phase contrast grating 4 precisely with such small dimensions, a production method described in greater detail below with reference to FIG. 2 is carried out.

Figure 3:
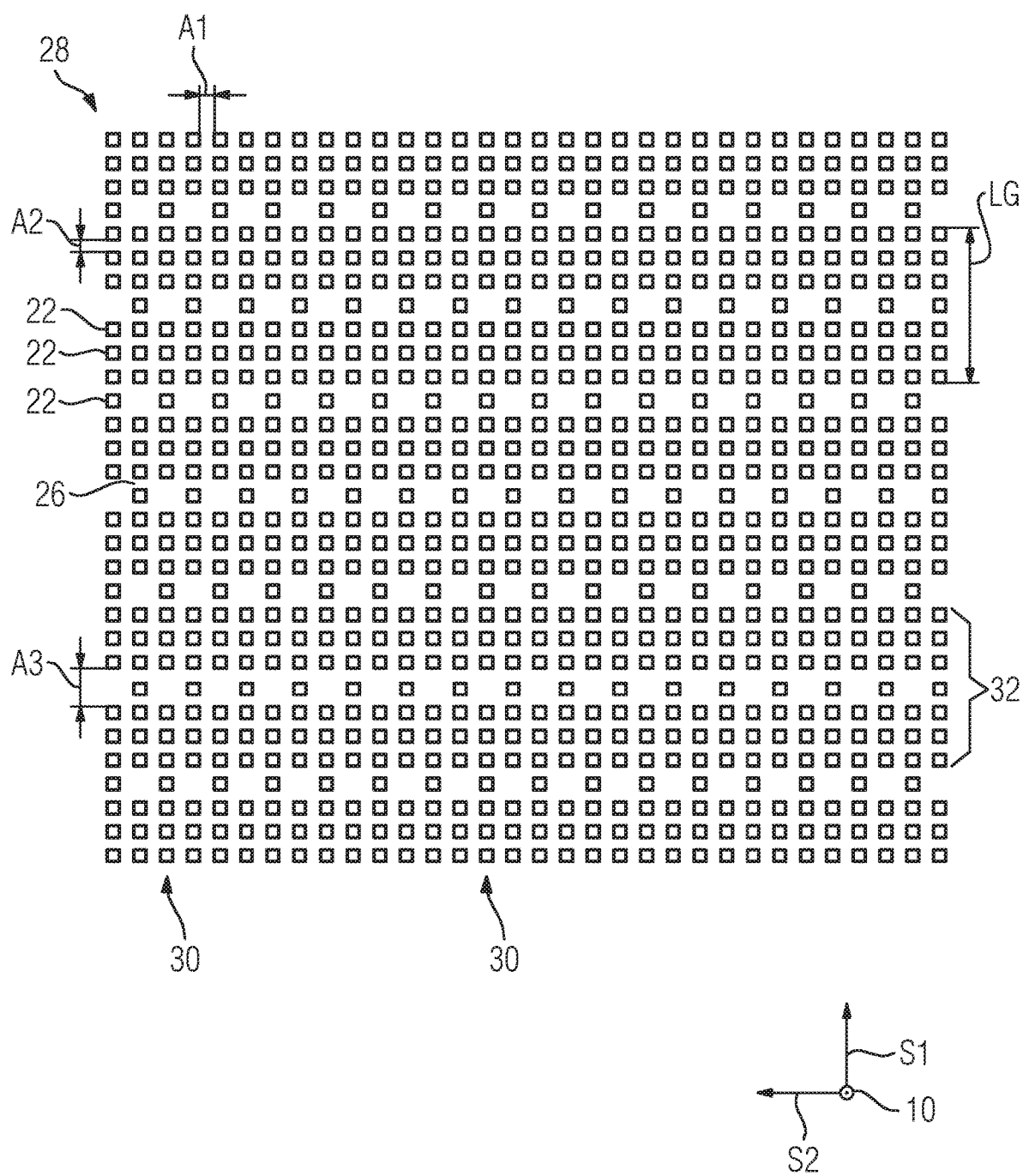
FIG. 3 shows a grid of injection structures for creating the phase contrast grating from a silicon substrate, in a schematic overhead view.

In a first method step 20, in this method injection structures 22 (see FIG. 3) are put into a first surface 24 (see FIG. 5) of a wafer-like silicon substrate 26 (with an initial thickness of more than 500 micrometers). In concrete terms the silicon substrate 26 involves a silicon wafer. The injection structures 22 in this case are distributed in a grid 28 over the first surface 24 of the silicon substrate 26. The grid 28 in this case is predetermined (in concrete terms in rows) in a first substrate direction S1 and a second substrate direction S2. I.e. the injection structures 22 are arranged in rows 30, which run in the first substrate direction S1 and repeat in the second substrate direction S2. In the row direction—i.e. in the first substrate direction S1—a number of injection structures 22 in each case (in the present example embodiment in concrete terms seven injection structures 22) are each combined into a group 32. The respective rows 30, in concrete terms the injection structures 22 arranged next to one another in the second substrate direction S2 are arranged in this case at a first distance A1 from one another. The first distance A1 amounts in the present example embodiment to 12 micrometers and in concrete terms corresponds in this case to a grating constant of the phase constant grating 4. Within the groups 32 the injection structures 22 are arranged at a second distance A2 from one another, which is smaller by a factor of 0.5 than the first distance A1.

The injection structures 22 are embodied square in this case with an edge length of less than or equal to 2 micrometers. A longitudinal extent LG of the groups 32 thus amounts to around 50 micrometers.

The groups 32 are also arranged at a third distance A3 from one another. The third distance A3 approximately corresponds in this case to leaving out one of the injection structures 22 in the respective row 30.

The injection structures 22 are subsequently expanded in the thickness direction 10 by way of an etching method into drilled holes, of which the side walls are perpendicular to the first surface 24. The so-called PAECE method ("photo assisted electro-chemical etching") method is used for this. In concrete terms the injection structures 22 are expanded into circular cylindrical drilled holes with a depth of 470 micrometers.

The second surface 34 lying opposite the first surface 24 is subsequently removed such that the drilled holes are opened on the rear side (i.e. towards the second surface 34). Etching methods such as for example wet-chemical etching with potassium hydroxide or plasma-induced dry etching are used to do this. In an area irradiated by the x-ray part beams 8 in the usage state as per specifications in the x-ray device 1, the thickness of the silicon substrate 26 subsequently amounts to 450 micrometers.

Figure 4:
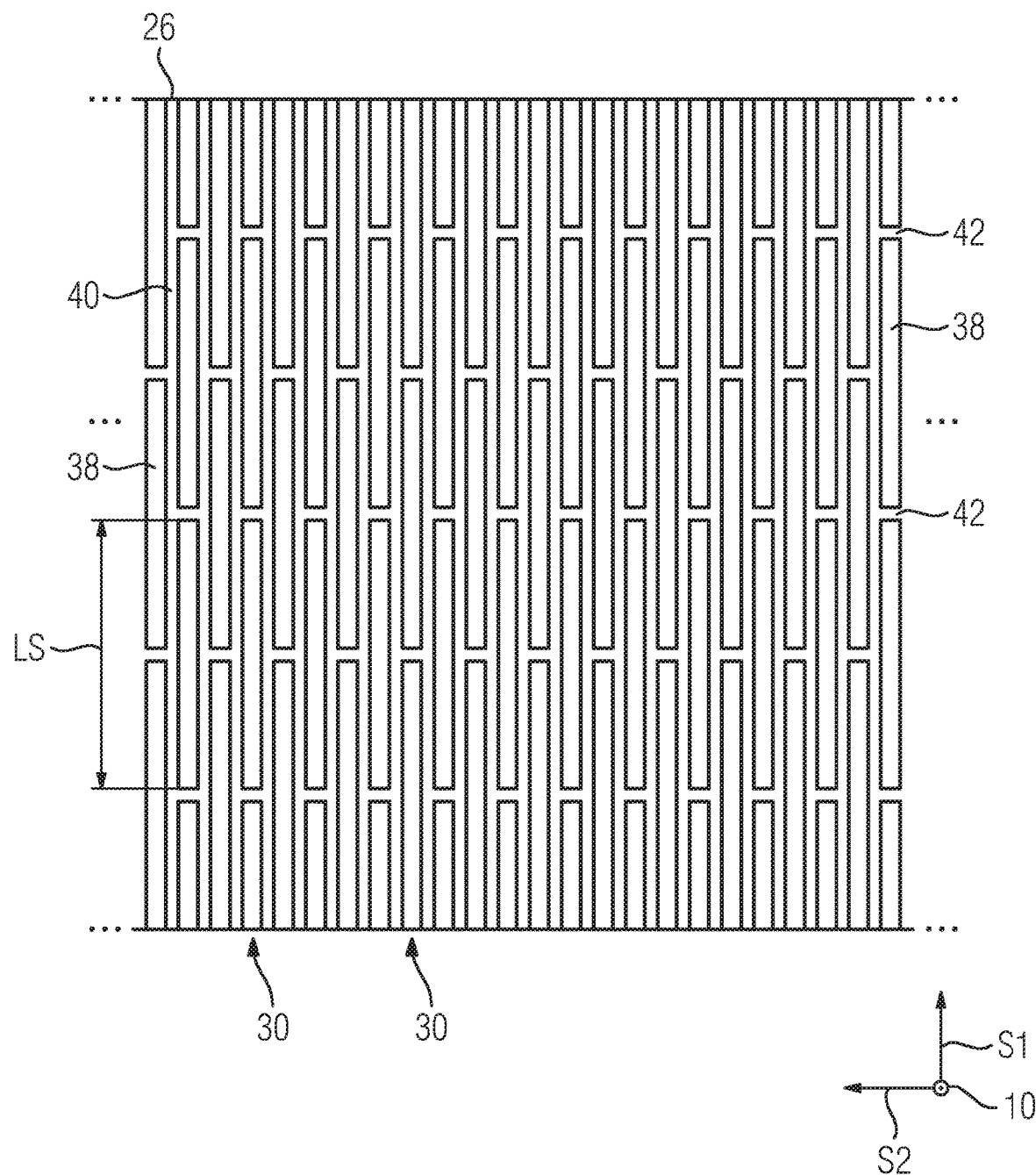
FIG. 4 shows columns formed from the grid in the silicon substrate, in a view in accordance with FIG. 3.

In a further etching step the drilled holes are alternately flushed from the first surface 24 and the second surface 34 with an etching medium acting anisotropically. The etching medium in this case contains potassium hydroxide, hydrogen peroxide and isopropanol. The first and the second substrate direction S1 or S2 are selected parallel to directions in which (111) crystal planes of the silicon pass through the (100) crystal plane (lying in parallel to the first surface 24). Through this the individual drilled holes are widened out in the first and second substrate direction S1 and S2, so that they have a square cross-section, and unite on continuing widening-out with the adjacent drilled holes within the respective groups 32 to a column 38 in each case (see FIG. 4, 5). Since the first distance A1 is greater than the second distance A2, longitudinal webs 40 made of silicon remain after the column formation between the individual rows 30. Because of the third distance A3 between the individual groups 32 a transverse web 42 also remains in each case, seen in the first substrate direction S1, between the columns 38 formed by the groups 32.

The grid 28 is selected in this case such that the columns 38 of two directly adjacent rows 30 formed are offset by half of their longitudinal extent LS in the first substrate direction S1. This means that the transverse webs 42 of two directly adjacent rows 30 are not aligned flush with one another. Instead the transverse webs 42 of the "next but one" rows 30 are always aligned flush with one another. This produces a good compromise between mechanical stability against bending about a bending axis aligned in the first substrate direction S1 and a sufficient flexibility for such bending.

In a second method step 50, the silicon substrate 26, in concrete terms the surfaces 24 and 34 as well as the inner walls of the columns 38, are pre-treated in order to prevent a chemical bonding between an x-ray-absorbing material to be poured into the column 38 in a subsequent method step 60, in concrete terms a tin alloy, and the inner walls and the surfaces 24 or 34.

To this end, in method step 60, the tin alloy is subsequently poured by way of a die casting method into the columns 38 for embodying the lamellae 6. The silicon substrate 26 thus forms a mold into which the tin alloy is introduced.

Figure 5:
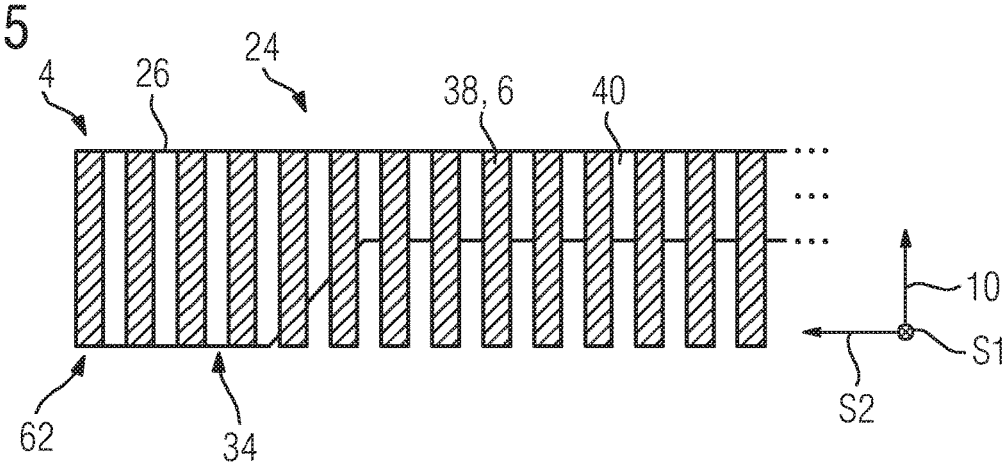
FIG. 5 shows the phase contrast grating in an intermediate production step, in a schematic sectional view.

As can be seen from FIG. 5, in an optional substep of method step 60, after the tin alloy has been poured in, in a further etching step (in an additional, optional method step) central areas of the rear side (i.e. on the side of the second surface 34) of the silicon substrate 26 in the thickness direction 10 are partly removed. Only in the second substrate direction S2 do terminal edge areas 62 (also: side areas) remain, so that in these edge areas 62 a more massive and thus more mechanically stable handling structure ("grip structure") is present. In concrete terms the edge areas 62 are masked accordingly before the etching. The etching is done by way of potassium hydroxide. The lamellae 6 formed by the tin alloy in the filled columns 38 are at least partly free after this step. Through this the flexural strength of the filled silicon substrate 26 about the bending axis running in the first substrate direction S1 is further reduced.

Optionally, within the framework of method step 60, there is also a cutting to size of the silicon substrate 26 to the dimensions required for the x-ray device 1 (not shown in any greater detail, optionally before the embodiment of the edge areas 62). In this case the first and the second substrate direction S1 or S2 are taken into account and where necessary markings are applied for adjustment. The cutting to size is carried out for example via laser beam cutting or wafer sawing.

Figure 6:
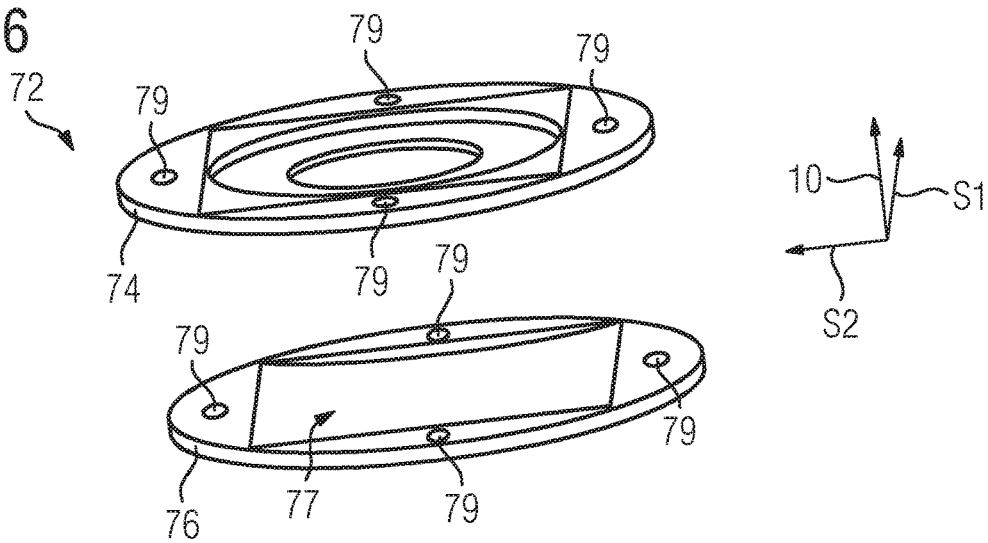
FIGS. 6 and 7 show a tool for remolding the phase contrast grating to a final contour, in different schematic perspective views in each case.
Figure 7:
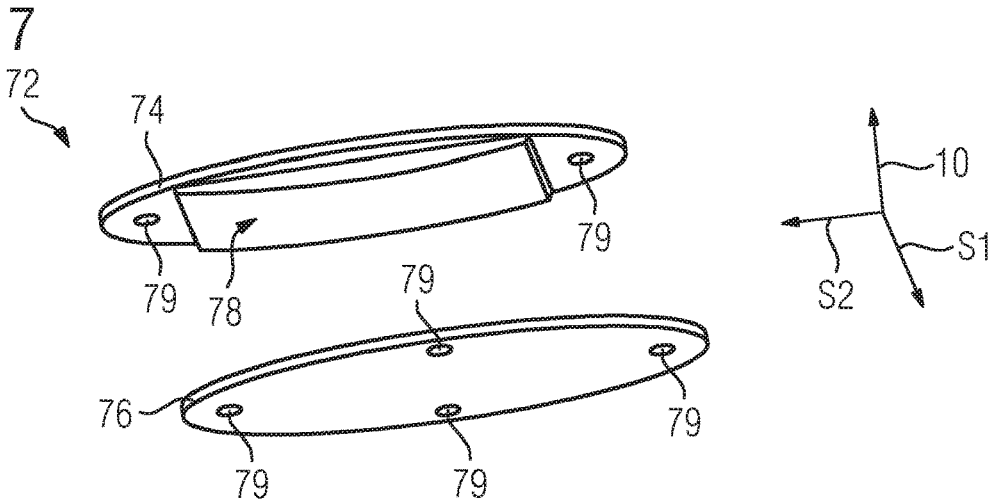

In a further method step 70, the silicon substrate 26 filled with the tin alloy is placed in a tool 72. The tool 72 is shown in greater detail in FIG. 6, 7 and has an upper shell 74 and a lower shell 76. Formed on the upper shell 76 are a lower shaping surface 77 and on the upper shell 74 an upper shaping surface 78. The two shaping surfaces 77 or 78 in this case are curved in a mirror image along a circular cylindrical outer surface. In concrete terms the lower shaping surface 77 is made as a concave shape into the lower shell 76. Accordingly the upper shaping surface 78 is embodied projecting as a concave shape from the upper shell 74. The radius of curvature of the two shaping surfaces 77 or 78 amounts to 300 millimeters in this case. The filled silicon substrate 26 in this case is inserted into the tool 72 such that the first substrate direction S1 is aligned parallel to the cylinder axis of the shaping surfaces 77 or 78. This produces the bending of the silicon substrate 26 about the bending axis aligned in the first substrate direction S1.

After the tool 72 has been closed, the upper shell 74 is "tensioned" against the lower shell 76 with weights or by springs such that a closing force, which corresponds to a mass of 50 grams, is produced.

The upper shell 74 and the lower shell 76 are made of an aluminum alloy. To close the tool 72, the upper shell 74 and the lower shell 76 are guided towards each other via guide pins, which are inserted into corresponding holes 79 of the upper shell 74 and the lower shell 76.

In a subsequent method step 80, the closed tool 72 (with the filled silicon substrate 26 inserted therein) is placed in an oven heated to 200 degrees Celsius. At this temperature value (also referred to as the "working temperature value"), under the closing force of the tool 72, creep (also referred to as "retardation") occurs in the tin alloy. I.e. the tin alloy, despite the slight closing force, undergoes a plastic deformation. Because of the rastering of the silicon substrate 26 described above with the columns 38, the flexural strength of the silicon substrate 26 is low enough for the silicon substrate 26, with creep of the tin alloy, to rest against the shaping surfaces 77 or 78. Because of the plastic deformation of the tin alloy, the contour of the silicon substrate 26 filled with the tin alloy predetermined by the shaping surfaces 77 or 78 will even be retained as the final contour after the opening of the tool 72.

Through the deformation described here, the lamellae 6 formed by the columns 38 filled with the tin alloy are aligned rotationally-symmetrically, so that a periodic, homogeneous x-ray absorption, which is matched to the radiation field—in concrete terms the respective x-ray part beam 8—is possible. Moreover the closing forces of the tool 72 as per specification lie outside of a range in which the longitudinal webs 40 and/or the transverse webs 42 would be mechanically damaged. Thus, with the creep remolding described above, no compression of the lamellae 6, but only the rotationally-symmetrical alignment about the first substrate direction S1 occurs. The latter can optionally be supported by the longitudinal webs 40 (and thereby also the transverse webs 42) projecting up to the rear-side surface 34 in the edge areas 62.

In an optional further method step, not shown in any greater detail, the silicon substrate 26 is removed at least to a large extent, so that "comb-like" lamellae 6 are left. For example, seen in the thickness direction 10, a remainder of the silicon substrate 26, which is short by comparison with the "height" of the lamellae 6 running in the thickness direction 10, is left in order to make it possible to geometrically hold the individual lamellae 6 together. This method step occurs in particular when the part removal in the substep described in FIG. 5 has not taken place. In a further example embodiment this method step also occurs in addition however, in order to expose the lamellae 6 even more.

Finally the phase contrast grating 4 formed by the lamellae 6 is built into the x-ray device 1.

The subject matter of the invention is not restricted to the example embodiments described above. Instead, further forms of embodiment of the invention can be derived by the person skilled in the art from the above description. In particular the individual features of the invention and their embodiment variants described on the basis of the different example embodiments can also be combined with one another in another way.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing a microstructure component, the method comprising:
    forming injection structures into a first surface of a wafer-like silicon substrate in rows, which run in a first substrate direction and repeat in a second substrate direction perpendicular to the first substrate direction, wherein respective rows arranged next to one another in the second substrate direction are arranged at a first distance from one another and respective injection structures arranged next to one another in the first substrate direction are arranged at a second distance from one another, which is smaller than the first distance;
    pouring a material for absorbing x-ray formed from the silicon substrate into a mold, the mold being at least deformable about a bending axis, formed by the silicon substrate, and including a plurality of cutouts running in a thickness direction of the silicon substrate with dimensions in the micrometer range;
    heating the mold, including the material poured into the mold, to a working temperature value below a melting temperature value of the material poured into the mold; and
    deforming the mold, with the material poured into the mold, into a final contour according to specifications, wherein the material for absorbing x-rays is introduced into the mold in a molten state, wherein at least a portion of the mold is removed in a thickness direction.

2. The method of claim 1, wherein the deforming includes deforming the mold into the contour according to the specifications by creep of the material poured into the mold.

3. The method of claim 2, wherein a value of 20 to 50 percent of the melting temperature value in Celsius is employed as the working temperature value.

4. The method of claim 2, wherein the mold is pre-treated before the pouring of the material for absorbing x-rays into the mold, to avoid a chemical bonding of the x-ray-absorbing material with the silicon substrate forming the mold.

5. The method of claim 2, wherein the deforming includes deforming the mold filled with the material via a tool including a lower shell and an upper shell with shaping surfaces, the shaping surfaces being complementary shapes including nesting concave and convex curves.

6. The method of claim 2, wherein for the deforming of the mold, a force corresponding to 0.1-1.5 N is exerted on the mold.

7. The method of claim 1, wherein a value of 20 to 50 percent of the melting temperature value in Celsius is employed as the working temperature value.

8. The method of claim 1, wherein the mold is pre-treated before the pouring of the material for absorbing x-rays into the mold, to avoid a chemical bonding of the x-ray-absorbing material with the silicon substrate forming the mold.

9. The method of claim 1, wherein the deforming includes deforming the mold filled with the material via a tool including a closed lower shell and a closed upper shell with nesting shaping surfaces, each curved in a same direction.

10. The method of claim 1, wherein for the deforming of the mold, a force corresponding to 0.1 to 1.5 N is exerted on the mold.

11. The method of claim 1, wherein the deforming of the mold is carried out in an oven by heating up to the working temperature value.

12. The method of claim 1, wherein the cutouts of the mold are formed by using etching technology to embody columns, which run in a first substrate direction and are separated from one another by transverse webs and are arranged like rows in parallel to one another in a second substrate direction, perpendicular to the first substrate direction.

13. The method of claim 12, wherein the columns, which follow one another in the second substrate direction, are arranged offset to one another in relation to their longitudinal extent in the first substrate direction.

14. The method of claim 1, wherein the cutouts are formed so as to penetrate the silicon substrate in the thickness direction.

15. The method of claim 1, wherein the cutouts have an aspect ratio in the thickness direction of around 1:450, and wherein the cutouts have a width of 1 to 4 micrometers.

16. The method of claim 1, wherein a value of 30 to 40 percent of the melting temperature value in Celsius is employed as the working temperature value.

17. The method of claim 1, wherein the material for absorbing x-rays is introduced into the cutouts of the mold in a molten state.

18. The method of claim 1, wherein groups of the injection structures are arranged at a third distance from one another, the third distance being larger than the first distance.

19. The method of claim 1, wherein the mold has a first surface on a front side and a second surface on a rear side opposite the first surface, the method further including removing at least a portion of the second surface such that drilled holes formed in the mold are opened on the rear side.

20. The method of claim 1, wherein columns of two directly adjacent rows are offset by half of their longitudinal extent in the first substrate direction, such that transverse webs of two directly adjacent rows are not aligned flush with one another.

* * * * *